(12) United States Patent
Laufer et al.

(10) Patent No.: US 8,765,260 B2
(45) Date of Patent: *Jul. 1, 2014

(54) BONDING AGENTS BASED ON CARBODIIMIDES, AQUEOUS RESORCINOL-FORMALDEHYDE-LATEX DISPERSIONS COMPRISING BONDING AGENT, ADHESION-IMPROVED FIBRES, PROCESSES FOR PRODUCTION THEREOF AND USE THEREOF

(75) Inventors: Wilhelm Laufer, Ellerstadt (DE); Anke Blaul, Darmstadt (DE); Armin Eckert, Oberhausen-Rheinhausen (DE); Andrea Fruth, Wiesbaden (DE); Ana Maria Cano Sierra, Heidelberg (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/215,269

(22) Filed: Aug. 23, 2011

(65) Prior Publication Data
US 2012/0100290 A1    Apr. 26, 2012

(30) Foreign Application Priority Data

| Aug. 30, 2010 | (EP) | 10174548 |
| Oct. 28, 2010 | (EP) | 10189268 |
| Nov. 22, 2010 | (EP) | 10192089 |
| Mar. 18, 2011 | (EP) | 11158813 |

(51) Int. Cl.
*C08K 5/29* (2006.01)
*B32B 9/00* (2006.01)

(52) U.S. Cl.
USPC .......................... 428/375; 524/195

(58) Field of Classification Search
USPC ........................................... 524/195; 428/375
See application file for complete search history.

(56) References Cited

U.S. PATENT DOCUMENTS

| 2,840,589 | A | 6/1958 | Smeltz |
| 3,661,623 | A | 5/1972 | Bhakuni et al. |
| 3,821,017 | A | 6/1974 | Bhakuni et al. |
| 3,867,181 | A | 2/1975 | Vizurraga |
| 4,159,363 | A | 6/1979 | Elmer et al. |
| 4,263,221 | A | 4/1981 | Schmabel et al. |
| 4,477,619 | A | 10/1984 | Lattimer et al. |
| 4,888,124 | A | 12/1989 | Blum et al. |
| 4,915,984 | A | 4/1990 | Murakami |
| 5,498,747 | A | 3/1996 | Pohl et al. |
| 6,310,125 | B1 * | 10/2001 | Rayner .................... 524/195 |
| 2002/0122938 | A1 * | 9/2002 | Fisher ....................... 428/375 |
| 2006/0094851 | A1 | 5/2006 | Audenaert et al. |
| 2008/0300347 | A1 | 12/2008 | Kurz et al. |

FOREIGN PATENT DOCUMENTS

| DE | 1130594 A | 5/1962 |
| EP | WO2010115684 A1 | 10/2010 |
| FR | 2009338 A1 | 5/1969 |

OTHER PUBLICATIONS

European Search Report from co-pending Application EP11177949 dated Sep. 29, 2011, 6 pages.

* cited by examiner

*Primary Examiner* — John Uselding
(74) *Attorney, Agent, or Firm* — Nicanor A. Kohncke

(57) ABSTRACT

The present invention relates to novel bonding agents based on carbodiimides, to aqueous resorcinol-formaldehyde-latex dispersion comprising bonding agent, to adhesion-improved fibres, to processes for production thereof, and to use thereof for improving adhesion in tyres.

10 Claims, No Drawings

BONDING AGENTS BASED ON CARBODIIMIDES, AQUEOUS RESORCINOL-FORMALDEHYDE-LATEX DISPERSIONS COMPRISING BONDING AGENT, ADHESION-IMPROVED FIBRES, PROCESSES FOR PRODUCTION THEREOF AND USE THEREOF

The present invention relates to novel bonding agents based on carbodiimides, to aqueous resorcinol-formaldehyde-latex dispersions comprising bonding agent, to adhesion-improved fibres, to processes for production thereof, and to use thereof for improving adhesion in tyres.

Carbodiimides are frequently used for the treatment of tyre cord, see U.S. Pat. No. 3,867,181 and DE-A-1770495. The said treatments are carried out in order to improve the hydrolysis resistance of PET fibres. DE-A-2326540 describes polyisocyanates which include polycarbodiimides. However, these processes are based on undesirable organic solvents and are uneconomic.

Resorcinol-formaldehyde-latex dispersions (RFL dip) have become particularly well established in the tyre sector, since they improve the adhesion of the synthetic textile (cord) to the rubber.

However, a disadvantage when polyester is used as cord material is that the adhesion-promoting properties of the RFL dip are inadequate.

Attempts have therefore been made to eliminate the said disadvantage by adding dimeric isocyanates, but these failed because of low performance levels and relatively low shelf life.

When polyester cord is used, isocyanates capped with caprolactams are added (see US A 20080300347) to the RFL dip in order to improve adhesion to the tyre/rubber. A disadvantage of these, in turn, is elimination of toxic monomeric isocyanates and caprolactam which has a disruptive effect in later stages of the process.

EP-A 2159241 moreover discloses the use of microencapsulated dimeric diphenylmethane 4,4'-diisocyanate and diphenylmethane 2,4-diisocyanate (MDI) to improve adhesion-promoting properties. However, the substances described in that document have the disadvantages of being expensive and not commercially available and of likewise being capable of eliminating toxic monomeric diisocyanates.

It was therefore an object of the present invention to provide bonding agents which in particular can be used to improve adhesion in resorcinol-formaldehyde-latex dispersions and which do not have the disadvantages of the prior art.

Surprisingly, it has now been found that novel bonding agents, comprising carbodiimized isocyanates and/or reaction products of these with surface deactivators, such as amines, provide excellent adhesion. These have the advantage that they do not eliminate any toxic monomeric isocyanates during processing in the later stages of the process, and can be produced by simple production methods.

The present invention therefore provides bonding agents, comprising at least one carbodiimide based on compounds of the formula (I)

in which
m is an integer from 1 to 500, preferably from 1 to 20,
$R=C_1-C_{18}$-alkylene, $C_5-C_{18}$-cycloalkylene, arylene and/or $C_7-C_{18}$-aralkylene,
R'=R—NCO, R—NHCONHR$^1$, R—NHCONR$^1$R$^2$ or R—NHCOOR$^3$ and
R"=—NCO, —NHCONHR$^1$, —NHCONR$^1$R$^2$ or —NHCOOR$^3$,
where R$^1$ and R$^2$ in R' are mutually independently identical or different and are a $C_1-C_6$-alkyl moiety, $C_6-C_{10}$-cycloalkyl moiety or $C_7-C_{18}$-aralkyl moiety, and R$^3$ is as defined for R$^1$ or is a polyester moiety or a polyamide moiety or —(CH$_2$)$_l$—(O—(CH$_2$)$_k$—O)$_g$—R$^4$, —C$_6$H$_4$(OH) or —C$_6$H$_3$(OH)—((CH)$_h$—C$_6$H$_4$(OH))$_y$,
where l=from 1 to 3, k=from 1 to 3, g=from 0 to 12, h=from 1 to 2 and y=from 1 to 50, and
R$^4$=H or $C_1-C_4$-alkyl,
where these have been surface-deactivated via reaction with at least one amine.

It is equally possible to use mixtures of carbodiimides of the formula (I), inclusive of the corresponding oligomers and/or polymers.

In one particularly preferred embodiment of the invention, the carbodiimides correspond to the formulae (II) to (IV)

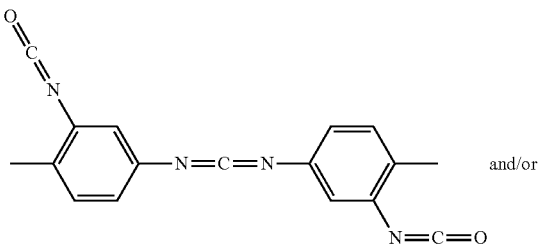

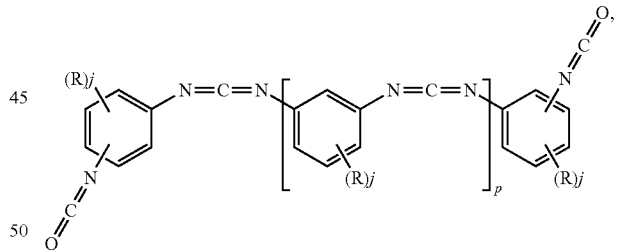

where $R=C_1-C_{18}$-alkylene, $C_5-C_{18}$-cycloalkylene, arylene and/or $C_7-C_{18}$-aralkylene
j is identical or different within the molecule and is from 1 to 5, and
p=from 0 to 500,
and/or sterically hindered carbodiimides of the formula (IV)

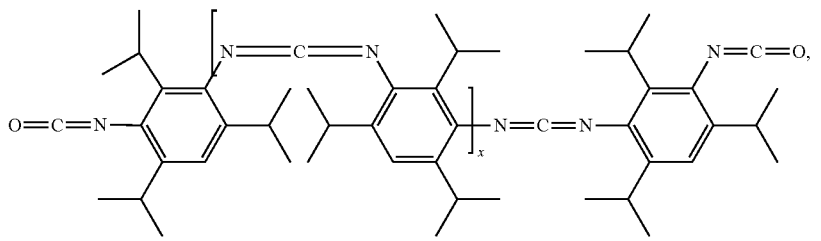

(IV)

where x=from 1 to 500, preferably from 1 to 50,
where these have been surface-deactivated via reaction with at least one amine.

As a result of the production process, the carbodiimides often occur in mixtures made of monomeric, oligomeric and/or polymeric carbodiimides. The said mixtures are within the subject matter of the invention.

It is equally possible to use compounds of the formulae (I) to (IV) which have been capped, e.g. with lactams, particularly preferably caprolactam, or with phenols, with novolacs, with resorcinol, with oxime and/or with epoxides.

The scope of the invention includes all of the abovementioned and hereinafter-listed moiety definitions, indices, parameters and explanations, which are either general or cited in preferred ranges and are in any desired combination with one another, i.e. also in any desired combination between the respective ranges and preferred ranges.

The compounds according to formula (I) to (IV) prior to the surface deactivation process are commercially available, e.g. from Rhein Chemie Rheinau GmbH, or can be produced by the processes familiar to the person skilled in the art, as described by way of example in DE-A-11 30 594 or U.S. Pat. No. 2,840,589, or via condensation of diisocyanates with elimination of carbon dioxide at elevated temperatures, e.g. at from 40° C. to 200° C., in the presence of catalysts. Examples of catalysts which have proved successful are strong bases or phosphorus compounds. It is preferable to use phospholene oxides, phospholidines or phospholine oxides, or else the corresponding sulphides. Other catalysts that can be used are tertiary amines, metal compounds which react as bases, metal salts of carboxylic acids, and non-basic organometallic compounds.

Suitable compounds for producing the carbodiimides and/or polycarbodiimides used are any of the diisocyanates, but for the purposes of the present invention it is preferable to use carbodiimides and/or polycarbodiimides which are based on $C_1$-$C_4$-alkyl-substituted aromatic isocyanates, e.g. tolylene 2,4-diisocyanate, tolylene 2,6-diisocyanate, a mixture made of tolylene 2,4-diisocyanate and tolylene 2,6-diisocyanate, hexamethylene diisocyanate, cyclohexane 1,4-diisocyanate, xylylene diisocyanate, isophorone diisocyanate, 2,6-diisopropylphenyl isocyanate, 2,4,6-triisopropylphenyl 1,3-diisocyanate, 2,4,6-triethylphenyl 1,3-diisocyanate, 2,4,6-trimethylphenyl 1,3-diisocyanate, 2,4'-diisocyanatodiphenylmethane, 3,3',5,5'-tetraisopropyl-4,4'-diisocyanatodiphenyl methane, 3,3',5,5'-tetraethyl-4,4'-diisocyanatodiphenylmethane, tetramethylxylene diisocyanate, naphthalene 1,5-diisocyanate, diphenyl methane 4,4'-diisocyanate, diphenylmethane 2,4'-diisocyanate, diphenylmethane 2,2'-diisocyanate, diphenyldimethylmethane 4,4'-diisocyanate, phenylene 1,3-diisocyanate, phenylene 1,4-diisocyanate, dicyclohexylmethane 4,4'-diisocyanate, dicyclohexylmethane 2,4'-diisocyanate, dicyclohexylmethane 2,2'-diisocyanate, methylcyclohexane diisocyanate, tetramethylxylylene diisocyanate, 2,6-diisopropylphenylene isocyanate and 1,3,5-triisopropylbenzene 2,4-diisocyanate or a mixture of these, or which are based on substituted aralkylene, e.g. 1,3-bis(1-methyl-1-isocyanatoethyl)benzene. It is particularly preferable that the carbodiimides and/or polycarbodiimides are based on tolylene 2,4-diisocyanate and tolylene 2,6-diisocyanate or on a mixture made of tolylene 2,4-diisocyanate and tolylene 2,6-diisocyanate.

In another embodiment of the present invention it is also possible to use a mixture of various carbodiimides.

It is particularly preferable that the particle size of the solid carbodiimides used is <50 µm.

In one embodiment of the invention, the bonding agents according to the invention can take the form of aqueous solution and/or aqueous dispersion and can also comprise further additives, e.g. rheology aids (antisettling agents), e.g. Borchi®Gel ALA (OMG Borchers GmbH) or Kelzan® S obtainable from Monsanto, or else Tragacanth, obtainable from R.T. Vanderbilt, stabilizers, emulsifiers, wetting agents and/or dispersing agents, e.g. Tamol® NN 9104 from BASF AG or Aerosol® OT45 from Cytec Surface Specialities GmbH, or Dispersogen® HR from Clariant International Ltd.

The proportions of carbodiimides in the aqueous dispersion are preferably from 1 to 80%, particularly preferably from 40 to 60%.

The carbodiimides according to the invention have been surface-deactivated according to the formulae (I) to (IV) via reaction with at least one amine.

The amine used for the surface-deactivation (microencapsulation) process can comprise any amino-functional compound. These are preferably polyfunctional primary and secondary amines, particularly preferably polyfunctional aliphatic amines. Amines suitable according to the invention are particularly those selected from the group of cyclic and aliphatic, straight-chain or branched ($C_2$-$C_{14}$)-alkylamines, -diamines and -polyamines, in particular ($C_1$-$C_{10}$)-alkylamines, -diamines and -polyamines, preferably ($C_2$-$C_6$)-alkylamines, -diamines and -polyamines, where there can be at least some, or else full, interruption of the alkyl chain by heteroatoms, in particular oxygen or sulphur, and/or where the alkyl chain can comprise further substituents, e.g. hydroxy groups, carboxy groups, halogen or the like.

The following compounds may be mentioned as examples of amines suitable according to the invention: 2-methylpentamethylene-1,5-diamine and its isomers and homologues, e.g. 1,6-hexamethylenediamine; di-sec-butylamine; ethylenediamine; 1,3-propylenediamine; diethylenetriamine; triethylenetetramine; 3,3'-dimethyl-4,4'-diaminodicyclohexylmethane; methylnonanediamine; isophoronediamine; 4,4'-diaminodicyclohexylmethane; alkanolamines and -diamines, e.g. ethanolamine and diethanolamine, and/or amidoamines.

Among these, particular preference is given to 2-pentatnethylene-1,5-diamine and its isomers and homologues, e.g. 1,6-hexamethylenediamine.

These are particularly preferably polyfunctional primary and secondary amines, particularly preferably polyfunctional aliphatic amines, e.g. Jeffamine® T 403 from Huntsman, diisopropanolamine from BASF AG, or amidoamines, such as Versamid® 140 from Cognis, or Euretek 505 from Witco. In particular, these are compounds having hydrophilic groups, e.g. in particular amino groups or hydroxy groups, where these can react with the free isocyanate groups of the solid diisocyanate and thus form a surface coating on the isocyanates, where this then deactivates the isocyanates, examples therefore being amines, diamines and polyamines.

In one preferred embodiment of the invention, the surface deactivation agent used comprises a low-molecular-weight mono-, di- or polyamine having one or more primary and/or secondary amino group(s), the amounts used thereof specifically being such that the degree of deactivation (DD), calculated as ratio of equivalents of amino groups of the surface deactivation agent to the isocyanate groups and/or carbodiimide groups of the carbodiimide requiring deactivation (n $NH_2$/n NCO), is from 0.2 to 8 equivalent %.

In particular, the molar mass of the surface deactivation agent can be up to MM 600 g/mol.

Preferred concentrations of surface deactivation agent (amine) here, based on the amount of bonding agent, are from 1 to 10% by weight, in particular from 2 to 5% by weight.

The surface deactivation process preferably takes place via addition of the amine to an aqueous dispersion of the carbodiimide which optionally also comprises dispersing agent and antisettling agent, with stirring and/or milling. However, it is also possible to carry out the surface deactivation process via addition of the amine to an organic dispersion of the carbodiimide, e.g. to alcohol, toluene, etc.

Commercially available machines can be used for the stirring/milling process, examples being bead mills, dissolvers and/or blade stirrers.

The deactivation of the carbodiimides takes place in a manner known per se, see in particular EP 0 205 970 A and U.S. Pat. No. 4,888,124, the entire content of which is incorporated herein by way of reference, e.g. via:
a) dispersion of the pulverulent solid carbodiimide in a solution of the amine or
b) addition of the amine or of a solution of the amine to a dispersion of the solid fine-particle carbodiimide.

This surface deactivation process can take place in water and/or in organic solvents.

The present invention further provides resorcinol-formaldehyde-latex dispersions comprising the bonding agents according to the invention of the formulae (I) to (IV).

For the purposes of the invention, a resorcinol-formaldehyde-latex dispersion is a dispersion of the individual components resorcinol and formaldehyde, and/or formaldehyde together with a precondensate made of resorcinol and formaldehyde (e.g. Rhenosin® T from Rhein Chemie Rheinau GmbH and Penacolite® 50 obtainable from Indspec Chemical Corp.) and of one or more of the latex dispersions mentioned hereinafter.

The latex dispersion used for the purposes of the invention can be any of the latices known in the prior art, e.g. XSBR latex (carboxylated styrene-butadiene copolymers), HSSBR latex (styrene-butadiene copolymers), nitrile-butadiene copolymers (NBR latex), CR latex (polychloroprene), PSBR latex (pyridine-styrene-butadiene copolymers) and/or acrylate latex (acrylate-only copolymers and styrene-acrylate copolymers) and/or styrene-butadiene-vinylpyridine copolymer latices, preference being given to styrene-butadiene-vinylpyridine copolymer latices (e.g. Pliocord VP 106, obtainable from Eliochem). These are commercially available substances obtainable by way of example from Polymer Latex GmbH or from Eliokem.

The resorcinol-formaldehyde-latex dispersion here is preferably obtained via stirring to incorporate a basic aqueous mixture made of resorcinol and formaldehyde, or preferably a basic aqueous mixture made of formaldehyde and of the precondensate of resorcinol and formaldehyde, in a basic aqueous latex mixture.

The ratio of resorcinol to formaldehyde is preferably from 1:1 to 2.5:1.

The ratio of latex, based on solids content thereof, to the condensate made of resorcinol and formaldehyde is preferably from 10:1 to 4:1, particularly preferably 6:1.

The aqueous basic solutions used are preferably aqueous sodium hydroxide and/or ammonium hydroxide solutions. Preferred pHs here are from 10 to 11.

The amounts preferably used of the carbodiimides and/or surface-deactivated carbodiimides here are from 0.5 to 10%, particularly from 5 to 8%, based on the solids content in the resorcinol-formaldehyde-latex dispersion.

The present invention further provides a process for producing the resorcinol-formaldehyde-latex dispersions according to the invention, where at least one of the bonding agents according to the invention, comprising at least one compound of the formula (I) to (IV), is incorporated by stirring into the resorcinol-formaldehyde-latex dispersion.

The present invention further provides a further process for producing the resorcinol-formaldehyde-latex dispersions according to the invention, comprising at least one of the surface-deactivated bonding agents according to the invention, where for the surface-deactivation process, at least one carbodiimide according to the formulae (I) to (IV) is deactivated with at least one amine either
a) via dispersion of at least one pulverulent carbodiimide according to the formulae) to (IV) in a solution of at least one amine or
b) via addition of at least one amine or one solution of at least one amine to a dispersion of at least one of the carbodiimides according to the formulae (I) to (IV), and then
is incorporated by stirring into the resorcinol-formaldehyde-latex dispersion, or the resorcinol-formaldehyde-latex dispersion is incorporated by stirring into these solutions from a) or b).

Commercially available mixing assemblies, e.g. stirred tanks and dispersers, are used here to incorporate the bonding agents according to the invention, comprising the carbodiimides and/or surface-deactivated carbodiimides, by stirring into the resorcinol-formaldehyde-latex dispersion, or to incorporate the resorcinol-formaldehyde-latex dispersion by stirring into the bonding agent according to the invention with the carbodiimides and/or with the deactivated carbodiimides.

The present invention further provides adhesive formulations comprising at least one aqueous resorcinol-formaldehyde-latex dispersion according to the invention and also at least one activator.

Examples of activators for the purposes of the invention are epoxides, such as glycidyl ether GE 500 from Raschig, or Bisphenol A Epoxynovolac from Editya Birla Chemical, etc.

To produce the adhesive formulations here, it is preferable that the bonding agents according to the invention comprising the carbodiimides of the formulae (I) to (IV), or the carbodiimides surface-deactivated via reaction of at least one amine, are incorporated by stirring into the resorcinol-formaldehyde-latex dispersion, and that the activator is then added, but without exclusion of any other addition sequence.

The present invention further provides processes for improving the adhesion of reinforcement fibres to crosslinked rubber or elastomers, where the reinforcement fibres (fibres, cord) are introduced into the adhesive formulation according to the invention and are then dried, or the reinforcement fibres (fibres, cord) are treated in one or more steps with one or more of the constituents of the adhesive formulation according to the invention.

In particular in the case of the last-mentioned treatment in a plurality of steps then using one or more constituents of the adhesive formulation according to the invention, the fibre can also be subjected to intermediate drying.

This process especially improves the bond strength between reinforcement fibres and elastomers in tyres, drive belts, conveyor belts and/or hoses.

To the extent that the abovementioned process according to the invention is carried out in a plurality of steps using one or more constituents of the adhesive formulation according to the invention, examples of possible embodiments are as follows:

by way of example, the reinforcement fibre can first be introduced into at least one epoxide and optionally dried, and then introduced into the resorcinol-formaldehyde-latex dispersion according to the invention, where this dispersion comprises at least one bonding agent according to the invention, i.e. at least one carbodiimide of the formulae (I) to (IV) after reaction with an amine, or the reinforcement fibre is first introduced into a dispersion made of at least one epoxide and of at least one bonding agent according to the invention, where this bonding agent comprises at least one carbodiimide of the formulae (I) to (IV) after reaction with an amine, and is optionally dried, and then is introduced into a latex dispersion which also comprises resorcinol and formaldehyde, or formaldehyde and a resorcinol-formaldehyde precondensate.

The crosslinked rubber or elastomer here is preferably styrene-butadiene rubber (SBR rubber), butadiene rubber (BR rubber), natural rubber (NR rubber), synthetic natural rubber (IR rubber), polyurethane elastomers, or any mixture thereof.

In the abovementioned cases it is possible to use either preactivated (pretreated) reinforcement fibres or else non-preactivated reinforcement fibres.

The preactivated (pretreated) reinforcement fibres are by way of example polyester- or aramid-based fibres which during their production (spinning) have been treated with a size. Examples of commercially available products are KoSa 793 and KoSa 748 from KoSa. In many cases, the sizes comprise epoxides.

The non-pretreated reinforcement fibres are by way of example polyester- or aramid-based fibres. An example of commercially available products is KoSa 792.

This invention also includes a process for improving the adhesion of reinforcement fibres to crosslinked rubber or elastomers, where preactivated (pretreated) reinforcement fibres are introduced into the aqueous resorcinol-formaldehyde-latex dispersion according to the invention and are then dried.

For the purposes of the invention, the term fibres means not only fibres but also yarns, cord, and also reinforcement textiles, based by way of example on polyester or aramid, e.g. inter alia polyethylene-terephthalate-based fibres.

The present invention also provides adhesion-improved fibres obtainable by bringing the activator-pretreated fibres into contact with at least one aqueous resorcinol-formaldehyde-latex dispersion according to the invention, or by bringing a non-pretreated fibre into contact with at least one adhesive formulation according to the invention, and subsequent drying (setting) at temperatures of from 180 to 260° C.

The present invention further provides the use of the resorcinol-formaldehyde-latex dispersion according to the invention optionally in the presence of activators to improve the bond strength between reinforcement fibres and elastomers in tyres, drive belts, conveyor belts and/or hoses, and also provides the use of a bonding agent according to the invention optionally in the presence of activators to improve the bond strength between reinforcement fibres and elastomers in tyres, drive belts, conveyor belts and/or hoses.

The invention also includes a process for forming tyres, drive belts, conveyor belts and/or hoses comprising the steps of adding the adhesion-improved reinforcement fibres according to the invention to said tyres, drive belts, conveyor belts and/or hoses.

The following examples serve to illustrate the invention, but without any resultant limited effect.

INVENTIVE EXAMPLES

Chemicals Used:
TDI carbodiimide, a carbodiimide according to formula (II) which optionally can comprise oligomer content,
Addolink® CBM, caprolactam-capped MDI (diphenyl-methane 4,4-diisocyanate), obtainable from Rhein Chemie Rheinau GmbH,
Tamol®NN 9104, wetting/dispersing agent, obtainable from BASF AG,
Borchi Gel® L 75, antisettling agent, obtainable from OMG Borchers GmbH,
Aerosol® OT 75, wetting/dispersing agent, obtainable from Cytec Surface Specialties GmbH,
Kelzan® S, antisettling agent, obtainable from Monsanto,
Jeffamin® T 403, polyetheramine, obtainable from Huntsman International LLC,
Penacolite® 50, a resorcinol-formaldehyde precondensate, obtainable from Indspec Chemical Corp, and also
Pliocord® VP 106, a styrene-butadiene-vinylpyridine copolymer latex having 41% solids content, obtainable from Eliokern.

Table 1 summarizes the amounts used to produce an aqueous dispersion:

TABLE 1

| Material | Ex. 1 | Ex. 2 |
|---|---|---|
| TDI carbodiimide | 80 | |
| Addolink ® CBM | | 100 |
| Tamol ® NN 9104 | 4.4 | |
| Aerosol ® OT 75 | | 2.4 |
| Water | 85.6 | 91 |
| Borchi Gel ® L 75 | 0.5 | |
| Jeffamin ® T 403 | 2.0 | |
| Kelzan ® S, 3% in water | | 9.0 |

The amounts used have been stated in parts by weight.

The method of producing the aqueous dispersions here was as follows:

Water and wetting/dispersing agent (Aerosol® OT 75 or Tamol®NN 9104) were combined and dissolved/mixed. TDI carbodiimide or Addolink® CBM was then added and the mixture was homogenized in a dissolver. In example 1 (Ex. 1) Jeffamin T 403 was then added and incorporated by mixing with avoidance of shear forces. Borchi Gel®L 75 or the freshly produced Kelzan® S preparation was then incorporated by mixing, and the mixture was homogenized.

Table 2 gives the constitutions of adhesive formulations for treating preactivated polyester fibres:

TABLE 2

| Material | Ex. 3 (inv) | Ex. 4 (CE) | Ex. 5(CE) |
|---|---|---|---|
| Aqueous TDI carbodiimide dispersion according to Ex. 1 | 28 | | |
| Aqueous Addolink ® CBM dispersion according to Ex. 2 | | 28 | |
| Water | 367.3 | 367.3 | 395.3 |
| Sodium hydroxide (10%) | 6 | 6 | 6 |
| Penacolite ® 50 | 42.4 | 42.4 | 42.4 |
| Formaldehyde (37%) | 20.5 | 20.5 | 20.5 |
| Pliocord VP 106 | 411 | 411 | 411 |
| Ammonia (25%) | 24.7 | 24.7 | 24.7 |

CE = comparativ example, inv = according to the invention;

the amounts used have been stated in parts by weight.

The treated fibres were predried at about 135'C for about 60 s, and the setting process took 120 s at 230° C.

Vulcanization and adhesion testing were carried out according to ASTM D 4393. The test elastomer mixture used was Dunlop SP 5320, obtainable from Dunlop, with an activator PET yarn. The results of adhesion testing are summarized in Table 3:

TABLE 3

| | | Examples | | |
|---|---|---|---|---|
| Test | Unit | TDI carbodiimide (Ex. 3) | Addolink CBM (Ex. 4) | without bonding agent (Ex. 5) |
| Strap peel test (degree of cover) | % | <10 | <10 | <10 |
| Strap peel test (adhesion) | N/2.5 cm | 250-300 | 250-300 | 200-250 |
| T test* | N | 121 | 122 | 115 |
| H test* | N | 121 | 117 | 110 |

*Average value from 10 measurements

The experiments clearly show that the bonding agents according to the invention exhibit extremely good adhesion, while being markedly easier to produce and therefore more cost-effective than the prior art and moreover eliminating no toxic monomeric isocyanates during the drying process for the purpose of heat-setting. The bonding agents according to the invention therefore have marked environmental and production-related advantages over the compounds known in the prior art.

What is claimed is:

1. An aqueous resorcinol-formaldehyde-latex dispersion comprising at least one bonding agent wherein the bonding agent comprises at least one carbodiimide, wherein the carbodiimide comprises compounds of the formulae II, III and IV

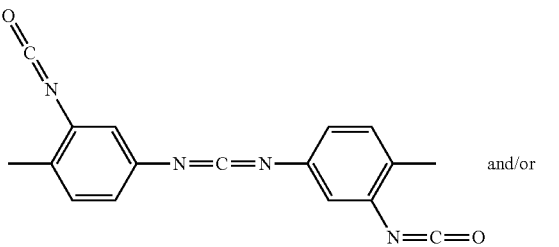

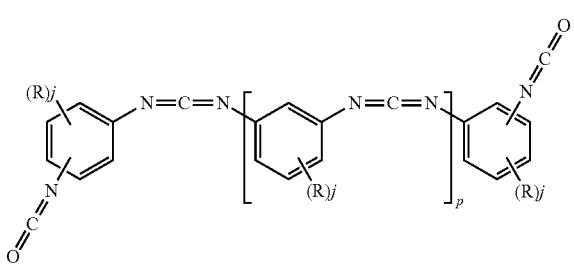

where R=$C_1$-$C_{18}$-alkylene, $C_5$-$C_{18}$-cycloalkylene, arvlene and/or $C_7$-$C_{18}$-aralkylene and j is identical or different within the molecule and is from 1 to 5, and p =from 0 to 500, and/or

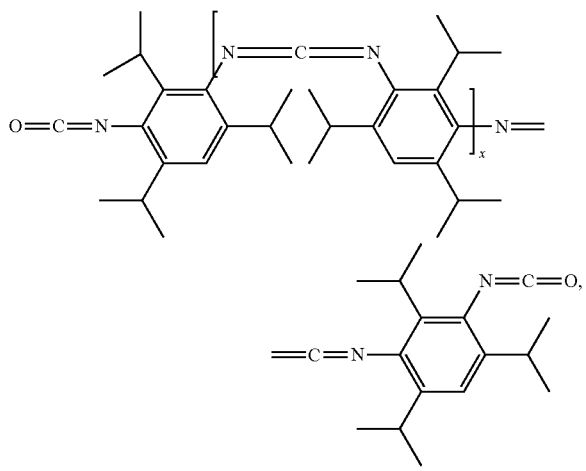

where x =from 1 to 500, and where these have been surface-deactivated via reaction with at least one amine.

2. An aqueous resorcinol-formaldehyde-latex dispersion according to claim 1, wherein the resorcinol-formaldehyde-latex dispersion comprises a dispersion of the individual components resorcinol and formaldehyde, and/or formaldehyde together with a precondensate made of resorcinol and formaldehyde and of one or more of the latex dispersions selected from the following group consisting of carboxylated styrene-butadiene copolymers (XSBR latex), nitrile-butadiene copolymers (NBR latex), polychloroprene (CR latex), pyridine-styrene-butadiene copolymers (PSBR latex), acrylate-only copolymers, styrene-acrylate copolymers (acrylate latex), and styrene-butadiene-vinylpyridine copolymer latices.

3. A process for producing aqueous resorcinol-formaldehyde-latex dispersions according to claim 1, comprising incorporating at least one bonding agent into the resorcinol-formaldehyde-latex dispersion by stirring.

4. A process for producing aqueous resorcinol-formaldehyde-latex dispersions according to claim 1 wherein the surface deactivation of the at least on carbodiimide according to formulae (II) to (IV) comprises incorporating at least one amine either
   a) via dispersion of at least one pulverulent carbodiimide according to the formulae (II) to (IV) in a solution of at least one amine or
   b) via addition of at least one amine or one solution of at least one amine to a dispersion of at least one of the carbodiimides according to the formulae (II) to (IV), and then
   by stirring into the resorcinol-formaldehyde-latex dispersion, or the resorcinol-formaldehyde-latex dispersion is incorporated by stirring into these solutions from a) or b).

5. Adhesive formulation, comprising an aqueous resorcinol-formaldehyde-latex dispersion according to claim 1 and at least one activator.

6. The adhesive formulation according to claim 5, wherein the activator is at least one epoxide.

7. A process for improving the adhesion of reinforcement fibres to crosslinked rubber and/or elastomers, comprising
   introducing the fibres into an adhesive formulation according to claim 5 and subsequently drying, or
   treating the fibres in one or more steps with one or more of the constituents of the adhesive formulation according to claim 5.

8. A process for improving the adhesion of reinforcement fibres to crosslinked rubbers or elastomers, comprising introducing preactivated fibres into an aqueous resorcinol-formaldehyde-latex dispersion according to claim 1 and subsequently drying.

9. Adhesion-improved fibres, obtainable by contacting activator-pretreated fibres with at least one aqueous resorcinol-formaldehyde-latex dispersion according to claim 1, or by contacting a non-pretreated fibre with at least one adhesive formulation according to claim 8 and subsequently drying (setting) at temperatures of from 180 to 260° C.

10. The aqueous resorcinol-formaldehyde-latex dispersion according to claim 1 wherein the amines comprises 1,6-hexamethylenediamine; di-sec-butylamine; ethylenediamine; 1,3-propylenediamine; diethylenetriamine; triethylenetetramine; 3,3'-dimethyl-4,4'-diaminodicyclohexylmethane; methylnonanediamine; isophoronediamine; 4,4'-diaminodicyclohexylmethane; alkanolamines and diamines.

* * * * *